United States Patent [19]

Schmitz et al.

[11] 4,021,455

[45] May 3, 1977

[54] PROCESS FOR THE MANUFACTURE OF ANTHRAQUINONESULPHONIC ACID

[75] Inventors: Reinold Schmitz, Blecher; Christoph M. Wittig, Leverkusen, both of Germany

[73] Assignee: Bayer Aktiengesellschaft, Leverkusen, Germany

[22] Filed: Dec. 22, 1972

[21] Appl. No.: 317,767

[30] Foreign Application Priority Data

Dec. 22, 1971 Germany .......................... 2163674

[52] U.S. Cl. .............................................. 260/370
[51] Int. Cl.² ...................................... C07C 143/38
[58] Field of Search ..................................... 260/370

[56] References Cited

UNITED STATES PATENTS

| | | | |
|---|---|---|---|
| 2,999,869 | 9/1961 | Donaldson | 260/370 |
| 3,873,581 | 3/1975 | Fitzpatrick et al. | 260/370 |

OTHER PUBLICATIONS

Zverev et al., Russian 142961 as cited in C.A. 56, 13979, 13980 (1961).
Kastal'skii et al., CA, 58, p. 3193 (1963).
Bvinov, Russian 128,864, as cited in C.A. 55, 2968 (1961).
Chem. Abstracts, vol. 68, p. 31630 (1968).

*Primary Examiner*—Jane S. Myers
*Attorney, Agent, or Firm*—Plumley and Tyner

[57] ABSTRACT

Process for the manufacture of practically mercury-free anthraquinonesulphonic acids, characterized in that anthraquinone is sulphonated with sulphuric acid containing $SO_3$ in the presence of catalysts containing mercury, at elevated temperature, the sulphonation mixture, if appropriate after dilution with water, is subsequently treated with an inorganic or organic compound of divalent sulphur and thereafter, if appropriate following dilution with water, the mercury compounds present in an insoluble form are separated off and the anthraquinonesulphonic acids are then isolated in a known manner.

7 Claims, No Drawings

PROCESS FOR THE MANUFACTURE OF ANTHRAQUINONESULPHONIC ACID

The subject of the present invention is a process for the maufacture of practically mercury-free anthraquinonesulphonic acids or of practically mercury-free solutions of antraquinonesulphonic acids in sulphuric acid, and practically mercury-free solutions of anthraquinonesulphonic acids in sulphuric acid manufactured in accordance with the process of the invention and practically mercury-free anthraquinonesulphonic acids, as well as practically mercury-free anthraquinonesulphonic acids, manufactured in accordance with the process of the invention, with anthraquinonesulphonic acids being understood, in particular, to denote anthraquinone-1-sulphonic acid, anthraquinone-1,5-disulphonic acid and anthraquinone-1,8-disulphonic acid and their mixtures, and sulphuric acid being understood to denote dilute or concentrated sulphuric acid optionally containing $SO_3$, and a process for reducing the mercury content of effluents which arise in the manufacture of anthraquinonesulphonic acids by sulphonation of anthraquinone with sulphuric acid containing $SO_3$ in the presence of catalysts containing mercury.

The process according to the invention for the manufacture of the anthraquinonesulphonic acids or their solutions is characterized in that anthraquinone is sulphonated with sulphuric acid containing $SO_3$ in the presence of catalysts containing mercury in a known manner at elevated temperature, the sulphonation mixture is thereafter treated, if appropriate after dilution with water, with inorganic or organic compounds of divalent sulphur at elevated temperature and following this, preferably after dilution with water, the insoluble compounds of mercury (especially HgS) thereby formed, and unreacted anthraquinone which may be present, are filtered off and thereafter the anthraquinonesulphonic acids are isolated from the practically mercury-free solutions in a known manner, for example by dilution of the melt with water or by addition of Na or K salts, such as NaCl or CKl. Preferably, the procedure followed is that the treatment with the inorganic or organic compounds of divalent sulphur is carried out in the undiluted sulphonation mixture and that after this treatment the mixture is diluted with water and filtered. If necessary, the treatment with the sulphur compounds is repeated.

The sulphonation of the anthraquinone is carried out in a known manner (compare Ullmanns Encyklopadie der technischen Chemic (Ullmann's Encyclopaedia of Industrial Chemistry), 3rd. edition, volume 3, page 666 ff (1953)).

Using this process, in which the catalysts are usually only employed once, solutions of anthraquinonesulphonic acids containing mercury, as well as anthraquinonesulphonic acids containing mercury and waste acids containing mercury, and therefore effluents containing mercury, are obtained.

In contrast, practically mercury-free anthraquinonesulphonic acids (Hg content in general < 10 ppm) and practically mercury-free effluents are obtained in the process according to the invention. The Hg content of the effluents declines from about 100 –300 ppm if the process according to the invention is not used, to between about 10 and < 1 ppm, the amount of effluent remaining the same, if the process according to the invention is used. Hence a further subject of the present invention is a process for reducing the mercury content of waste acids or effluents which arise in the manufacture of anthraquinonesulphonic acids by sulphonation of anthraquinone with sulphuric acid containing $SO_3$ in the presence of catalysts containing mercury, which is characterized in that the sulphonation mixtures are treated, if appropriate after dilution with water, with inorganic or organic compounds of divalent sulphur at elevated temperature and following this insoluble mercury compounds formed are filtered off, preferably after dilution with water, and the sulphonic acids are isolated in a known manner.

The treatment of the sulphonation melt with the reagents containing sulphur is carried out at temperatures of about 20°–180° C, preferably between 70° and 150° C.

The duration of treatment if generally about ½–2 hours.

Possible reagents are: inorganic compounds of divalent sulphur for example, sulphur-phosphorus compounds such as $P_4S_3$, $P_4S_5$, $P_4S_7$ and $P_4S_{10}$.

Examples of organic compounds of divalent sulphur which are used are thiourea, 1,3,5-trithiane and thio-organic carboxylic acids and their derivatives such as thioacetic acid, thioacetamide, thioformamide and thiobenzamide. The thio organic carboxylic acids and their derivatives have been found to be particularly suitable.

Of course, mixtures of the reagents mentioned can also be used, or various reagents can be used in succession. The amount of the reagents to be employed depends on the amount of mercury or mercury compounds present in the sulphonation mixture. In general, one to five times the amount of the reagents which is equivalent to the amount of mercury present is employed. However, an excess of the reagents does not adversely affect the process.

After dilution with water, the entire amount of mercury can be filtered off from the reaction mixture treated in accordance with the process. In individual cases it can be advisable to complete the precipitation of the mercury, after dilution by means of a suitable reagent; for example, the treatment of the undiluted melt with thioureas is suitably followed by a treatment of the diluted melt with phosphorous acid;

Since the HgS which as a rule is present as the insoluble mercury compound tends to form colloidal solutions, it can be appropriate to facilitate the filtration by using suitable filtration aids, for example by means of active charcoal, kieselguhr, asbestos powder or the like. Furthermore it can be advisable, for technical reasons, to follow a coarse filtration, which, for example, removes the anthraquinone together with the bulk of the mercury, by a fine filtration for example over filter plates containing asbestos or other finely porous materials, and thereby to remove the remainder of the mercury compounds from the solutions of the anthraquinone-sulphonic acids. The removal of the insoluble Hg compounds can also be effected by other processes of solid-liquid separation, for example by centrifuging.

All the temperature data are in ° C.

EXAMPLE 1

100 ml of 20% strength oleum, 0.84 g of $Hg_2SO_4$ and 160 g of anthraquinone are sulphonated for 3 hours at 120° C; thereafter, 0.5 g of thioacetamide is added and the treatment is continued for 30 minutes at 120° C. The melt is then diluted with 900 ml of water and thereafter stirred for 1 hour at the reflux temperature, and the unsulphonated anthraquinone is removed at 80° C by filtration through Seitz K7 filter plates and rinsed with 180 ml of water. 76 g of anthraquinone, containing 6.5% of mercury as HgS, are recovered. 1 ppm of Hg remains in the solution of the anthraquinone-1-sulphonic acid.

EXAMPLE 2

The sulphonation is carried out analogously to Example 1. If instead of the thioacetamide 0.5 g of sulphur is employed, an anthraqiunone-1-sulphonic acid solution containing 6 ppm of Hg is obtained.

EXAMPLE 3

If the sulphonated melt is treated with 4 g of $Na_2S_2O_3$, the Hg content in the solution of the antraquinone-1-sulphonic acid is reduced to 14 ppm of Hg.

EXAMPLE 4

The sulphonation is carried out in accordance with Example 1. If instead of the thioacetamide 4 ml of thioacetic acid are employed, an anthraquinone-1-sulphonic acid solution containing 0.3 ppm of Hg is obtained.

EXAMPLE 5

The sulphonation is carried out in accordance with the process described in Example 1. If instead of the thioacetamide 1 g of thiourea is used and the melt, diluted with 900 ml of water, is subsequently treated with 5 ml of 80% strength $H_3PO_3$ for 1 hour at the reflux temperature, the anthraquinone-1-sulphonic acid solution contains 4 ppm of Hg.

EXAMPLE 6

If, in the sulphonation according to Example 1, 0.5 g of $P_2S_5$ is employed instead of the thioacetamide, an antraquninone-1-sulphonic acid solution containing 0.5 ppm of Hg is obtained.

EXAMPLE 7

The sulphonation is carried out as described in Example 1 and the thioacetamide is replaced by 1 g of $P_2S_5$.

The anthraquinone-1-sulphonic acid solution (0.2 ppm of Hg) is precipitated with 180 ml of 25% strength KCl solution at 98°–100° C, the mixture is stirred for a further 30 minutes and is left to cool to 60° c, and the product is filtered off, washed with 5% strength KCl solution and dried. The 97 g of potassium anthraquinone-1-sulphonate thus obtained contain 1 ppm of Hg.

EXAMPLE 8

100 ml of 20% strength oleum, 0.84 g of $Hg_2SO_4$ and 160 g of anthraquinone are sulphonated for 3 hours at 120° C, the mixture is then diluted with 900 ml of water and the anthraquinone which has not been sulphonated is filtered off at 80° C and washed with 180 ml of water. 0.5 g of $P_2S_5$ is added to the anthraquinone-1-sulphonic acid solution and the mixture is heated to the reflux temperature for 1 hour and filtered at 80° C through a Seitz K7 filter plate. The solution of the anthraqunone-1-sulphonic acid contains 40 ppm of Hg. If, in this example, the $P_2S_5$ is replaced by 0.5 g of thioacetamide, the solution of the anthraquinone-1-sulphonic acid contains 52 ppm of Hg.

EXAMPLE 9

2.5 g of $Hg_2SO_4$ and 208 g of anthraquinone are added to 180 ml of 20% strength oleum and 70 ml of 65% strength oleum and sulphonation is carried out for 3 hours at 140° C. After cooling to 100° C, 2.5 g of $P_2S_5$ are added to the melt and the whole is stirred for a further 30 minutes at 100° C. The melt is filtered off on a G3 frit at 90° C and the product is washed with 120 ml of 79% strength $H_2SO_4$. The anthrqunine-1,5-disuphonic acid isolated thereby is dissolved in 700 ml of water at 100° C and the solution is filtered at 80° C through a Seitz K7 filter plate. The anthraquinone-1,5-disulphonic acid solution contains 2 ppm of Hg.

The sodium salt of anthraquinone-1,5-disulphonic acid which is obtained by dropwise addition of 350 ml of saturated NaCl solution at 95° C to the solution of the disulphonic acid, filtration at 75° C, washing with 5% strength NaCl solution and drying, contains 20 mmp of Hg (157 g yield).

The mother liquor obtained after filtration through the G3 frit contains anthraquinone-1,8-disulphonic acid. The acid is diluted with 800 ml of water and filtered at 80° C through a K7 filter plate. The solution contains 200 ppm of Hg. The potassium salt is obtained by precipitation with 300 ml of 25% strength KCl at 90°–98° C, filtration at 70° C and washing with 5% strength KCl solution. It contains 260 ppm of Hg (96 g yield).

If the anthraquinone-1,8-disulphonic acid dissolved in 800 ml of water is subjected to an after-treatment with thioacetamide, by adding 2.5 g thereof and stirring the mixture for 30 minutes at 100° C, the Hg content is reduced to 3 ppm. The dried potassium salt then contains 6 ppm of Hg.

EXAMPLE 10

2.5 g of mercury-(I) sulphate and 208 g of anthraquinone are introduced into 180 ml of 20% strength oleum. After adding 70 ml of 65% strength oleum the reaction mixture is heated to 140° C for 4 hours, whilst stirring. It is thereafter cooled to 120° C and 1.9 g of thioacetamide are then added. This temperature is maintained for half an hour. 26.7 ml of water are then added dropwise. The reaction mixture is now slowly cooled to 90° C and filtered on a glass suction filter. The filter cake is washed with 120 ml of 78% strength sulphuric acid.

The anthraquinone-1,5-disulphonic acid obtained as the residue is dissolved in 700 ml of water. After filtration through a Seitz K7 filter at 95° C, the solution contains 6.5 ppm of mercury. 350 ml of saturated sodium chloride solution are added dropwise at the same temperature. The salt which precipitates is filtered off at 75° C, washed with 6% strength sodium chloride solution until neutral and dried. Yield: 160 g. The sodium anthraquinone-1,5-disulphonate contains 17 ppm of mercury.

The filtrate together with the wash acid, which contains the anthraquinone-1,8-disulphonic acid, is diluted with 960 ml of water and stirred for 2 hours at 100° C. After filtration through a Seitz filter K7 at 100° C, this solution contains 0.1ppm of mercury. 300 ml of saturated potassium chloride solution are added dropwise at 9:°–98° C. The salt which precipitates is filtered off at 70° C on a glass suction filter, washed with 5% strength potassium chloride solution until nuetral and dried. Yield: 93 g. The potassium anthraquninone-1,8-disulphoate contains 0.3 ppm of mercury.

EXAMPLE 11

If in Example 10 2.24 g of phosphorus pentasulphide are used instead of thioacetamide, the solution of te anthraquinone-1,5-disulphonic acid, after filtration through a Seitz filter K7, contains 3.7 ppm of mercury and the sodium anthraquinone-1,5-disulphonate precipitaed therefron contains 13 ppm of mercury. Yield 149 g.

The solution of anthraquinone-1,8-disulphonic acid, diluted with water, is filtered through a Seitz filter K7 immediately after heating to 100° C. Thereafter, it contains 55 ppm of mercury and the potassium anthraquinone-1,8-disulphonate precipitated therefrom contains 200 ppm of mercury. Yield: 92 g.

If on the other hand, before dilution with water, 1.1 g of phosphorus pentasulphide are added to the filtrate, together with the wash acid, which contains the anthraquinone-1,8-1 -disulphonic acid, at room temperature, and subsequently 960 ml of water are added dropwise, the solution, after heating to 100° C and filtration through a Seitz filter K7 only contains 0.9 ppm of mercury and the potassium anthraquinone-1,8-disulphonate precipated therefrom contains 1 ppm of mercury.

EXAMPLE 12

100 ml of 20% strength oleum, 0.84 g of $Hg_2SO_4$ and 160 g of anthraquinone are mixed and heated to 120° C for 3 hours. 150 ml of water are added dropwise, during which the temperature is allowed to rise to at most 150°, the batch is then stirred until any lumps which may have been produced have again been stirred up well, 0.3 g of $P_2S_5$ is added and the temperature is kept at 120° for 1 hour; the mixture is then diluted with 750 ml of water and heated to the refluxing temperature for 1 hour. If now the recovered quinone which has precipitated is separated off and the resulting solution of the anthraquinone-1-sulphonic acid is clarified by filtration through a Seitz K 7 filter plate, the clarified solution retains 0.6 ppm of Hg.

We claim:
1. In the process of preparing a solution of anthraquinone-sulphonic acid by sulfonating anthraquinone in the presence of mercury-containing catalyst in which a crude undiluted solution containing antraquinone-sulfonic acid and mercury or mercury containing compounds is obtained; the improvement comprising reducing the content of said mercury or mercury compounds in said crude undiluted solution by:
   1. treatment of the crude undiluted solution with a sulfur-containing compound selected from the group consisting of $P_4S_3$, $P_4S_5$, $P_4S_7$, $P_4S_{10}$, thioacetic acid, thioformamide, thiourea, thionenzamide, and 1,3,5-trithiane under conditions effective to form an insoluble mercury compound; and then
   2. removing said insoluble mercury compound.
2. The process of claim 1 in which the step (1) of treatment with a sulfur-containing compound is carried out at 70°–180° C.
3. The process of claim 1 in which said sulfur-containing compound is $P_4S_3$, $P_4S_5$, $P_4S_7$ or $P_4S_{10}$.
4. The process of claim 1 in which said sulfur-containing compound is thioacetic acid, thioacetamide, thioformamide, thiobenazmide or thiourea.
5. The process of claim 1 in which said sulfur-containing compound is thioacetamide.
6. The process of claim 1 in which said sulfur-containing compound is $P_4S_{10}$.
7. The process of claim 1 in which said step (2) removing said insoluble mercury compound is carried out after the crude undiluted solution treated with a sulfur-compound is diluted with water.

* * * * *